(12) United States Patent
Dusterhoft et al.

(10) Patent No.: US 11,980,398 B2
(45) Date of Patent: May 14, 2024

(54) CROSSLINK LOCKING MECHANISM

(71) Applicant: Astura Medical Inc., Iriving, TX (US)

(72) Inventors: Ross Dusterhoft, Irving, TX (US);
Thomas Purcell, Irving, TX (US)

(73) Assignee: ASTURA MEDICAL INC, Irving, TX (US)

( * ) Notice: Subject to any disclaimer, the term of this patent is extended or adjusted under 35 U.S.C. 154(b) by 0 days.

(21) Appl. No.: 17/989,627

(22) Filed: Nov. 17, 2022

(65) Prior Publication Data

US 2023/0149051 A1 May 18, 2023

Related U.S. Application Data

(60) Provisional application No. 63/280,985, filed on Nov. 18, 2021.

(51) Int. Cl.
*A61B 17/70* (2006.01)
(52) U.S. Cl.
CPC ................ *A61B 17/7052* (2013.01)
(58) Field of Classification Search
CPC .............. A61B 17/705; A61B 17/7049; A61B 17/7052
See application file for complete search history.

(56) References Cited

U.S. PATENT DOCUMENTS

| | | | | |
|---|---|---|---|---|
| 5,167,662 A | * | 12/1992 | Hayes ................ | A61B 17/7076 606/151 |
| 2005/0090821 A1 | * | 4/2005 | Berrevoets ......... | A61B 17/7052 606/252 |
| 2006/0195095 A1 | * | 8/2006 | Mueller ............. | A61B 17/7052 606/252 |
| 2012/0083889 A1 | | 4/2012 | Purcell | |
| 2012/0271419 A1 | | 10/2012 | Merik | |
| 2014/0296917 A1 | | 10/2014 | Donner et al. | |
| 2015/0164557 A1 | * | 6/2015 | Fauth ................. | A61B 17/1671 606/269 |

OTHER PUBLICATIONS

International Search Report and Written Opinion in PCT Application No. PCT/US22/50320 dated Feb. 22, 2023.

* cited by examiner

*Primary Examiner* — Tessa M Matthews
(74) *Attorney, Agent, or Firm* — Michael R. Shevlin

(57) ABSTRACT

A crosslink mechanism features a locking clip with interlocking teeth. When being deployed, the surgeon will compress the spring loaded clips, freeing rotation on both sides of the mechanism. Once clipped onto the sequential reducers, the surgeon releases the clips allowing the spring to lock the teeth and therefore lock rotational freedom out of the mechanism.

16 Claims, 4 Drawing Sheets

CROSSLINK LOCKING MECHANISM

CROSS-REFERENCE TO RELATED APPLICATIONS

This application claims the benefit of U.S. Provisional Application No. 63/280,985 filed Nov. 18, 2021, which is incorporated herein by reference.

FIELD

The present invention relates generally to the field of surgery, and more specifically, to crosslink locking mechanism for use with reducers in spinal fusion surgery.

BACKGROUND

The spine is a series of individual bones called vertebrae. A normal spine has no side-to-side curve but does have a series of front-to-back curves, giving it a gentle "S" shape. Many people have an abnormal curvature of the spine and it may be necessary to straighten or adjust the spine into a proper curvature and alignment.

Spinal surgical procedures have been developed to correct the abnormal curvature of the spine. One procedure involves placing multiple pedicle screws into the vertebrae of the curved region and coupling spinal fixation rods to the screw heads. The rods are shaped to mimic the normal curvature and force the spine into proper alignment once positioned within the screw head. The rods are then secured or locked to the screws maintain the curvature.

The Spinal surgical procedures can require complex movement and manipulation of the vertebrae to restore normal curvature to the patient. The manipulation may include a rotational force applied on pedicle screws in the coronal plane (medial-laterally) is referred to as "derotation". This is usually done by applying compression and/or distraction forces of a derotation instrument to vertebrae via the screw extenders.

Typically there is a derotation instrument on each side of the spine that are connected with a crosslink between them. Current crosslink either do not lock rotational freedom or require the turning of a knob or bolt. Traditional crosslink locking mechanisms often require a knob, bolt, or screw to lock or tighten the rotational/hinge freedom of the device. These crosslink locking mechanisms are slow due to the requirement of turning of a knob or bolt, and some require the surgeon to tighten the device either by hand or with a secondary instrument.

The speed of this operation is of high importance A faster, more convenient method of locking rotational motion is needed.

Accordingly, there remains a need for instruments and methods that provide solutions to the problems of current systems. The present invention is directed toward meeting these needs.

SUMMARY

The present invention is directed to a crosslink mechanism features a locking clip with interlocking teeth. When being deployed, the surgeon will compress the spring loaded clips, freeing rotation on both sides of the mechanism. Once clipped onto the sequential reducers, the surgeon releases the clips allowing the spring to lock the teeth and therefore lock rotational freedom out of the mechanism.

DETAILED DESCRIPTION

Figure 1A:
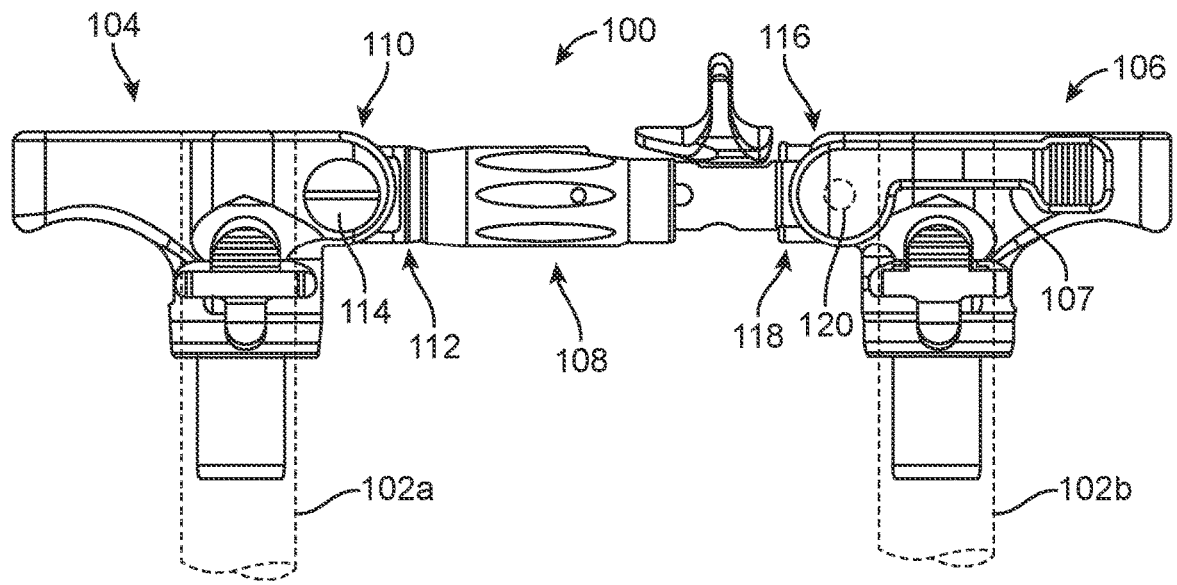
FIGS. 1A and 1B show a side view and top view of one embodiment of a crosslink that is configured to rigidly couple with spinal screw reducers or extenders.

Reference will now be made in detail to the present embodiments of the technology, examples of which are illustrated in the accompanying drawings. Similar reference numbers may be used to refer to similar components. However, the description is not intended to limit the present disclosure to particular embodiments, and it should be construed as including various modifications, equivalents, and/or alternatives of the embodiments described herein.

It will be understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be further understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

The expression "configured (or set) to" used in the present disclosure may be used interchangeably with, for example, the expressions "suitable for", "having the capacity to", "designed to", "adapted to", "made to" and "capable of" according to a situation. The expression "configured (or set) to" does not mean only "specifically designed to" in hardware. Alternatively, in some situations, the expression "a device configured to" may mean that the device "can" operate together with another device or component.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. For example, it will be appreciated that all features set out in any of the claims (whether independent or dependent) can be combined in any given way.

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Figure 1B:
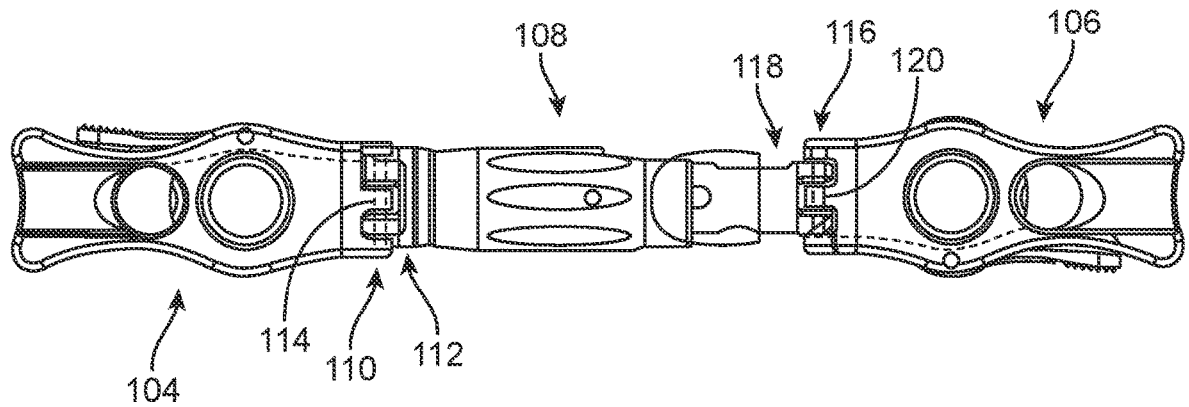

FIGS. 1A and 1B show a side view and top view of one embodiment of a crosslink 100 that is configured to rigidly couple with spinal screw reducers or extenders 102, such as sequential screw reducers, to correct a rotation deformity of the spine by turning or rotating the deformed spine structure toward a normal position. The crosslink 100 includes a left connector 104, a right connector 106, and a connecting member 108. The crosslink 100 can be adjusted to many different orientations. The left and right connectors 104, 106 are configured to rotate with respect to the connecting member 108. Connecting member 108 may also be shortened or extended are needed. The connecting member 108 includes a center locking mechanism that rigidly locks the length between the two locking clips. It is important that this length is locked down for the locking clips to function For rotation, the left connector 104 includes a left connector hinge 110 that is rotatably coupled to a left connector hinge 112 of the connecting member 108 by a left hinge pin 114. A left locking system 200 is configured to lock the left connector 104 to the left end of the connecting member 108. The right connector 106 includes a right connector hinge 116 that is rotatably coupled to a right connector hinge 118 of the connecting member 108 by a right hinge pin 120. A right locking system 300 is configured to lock the right connector 106 to the right end of the connecting member 108.

Figure 2A:
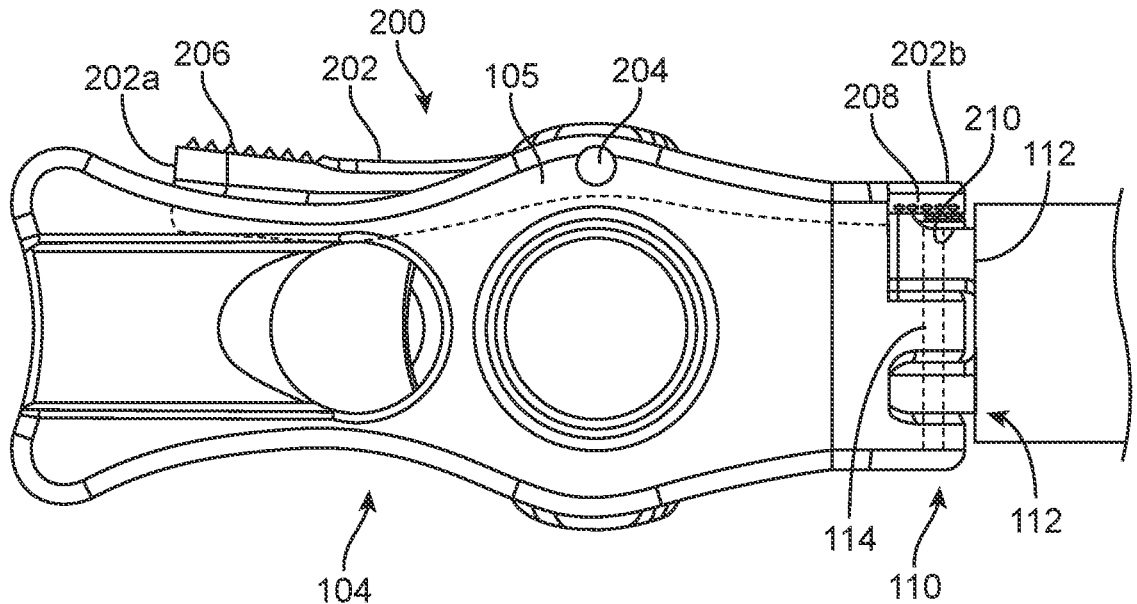
FIGS. 2A and 2B show a left locking system configured to lock the left connector to the left end of the connecting member.
Figure 2B:
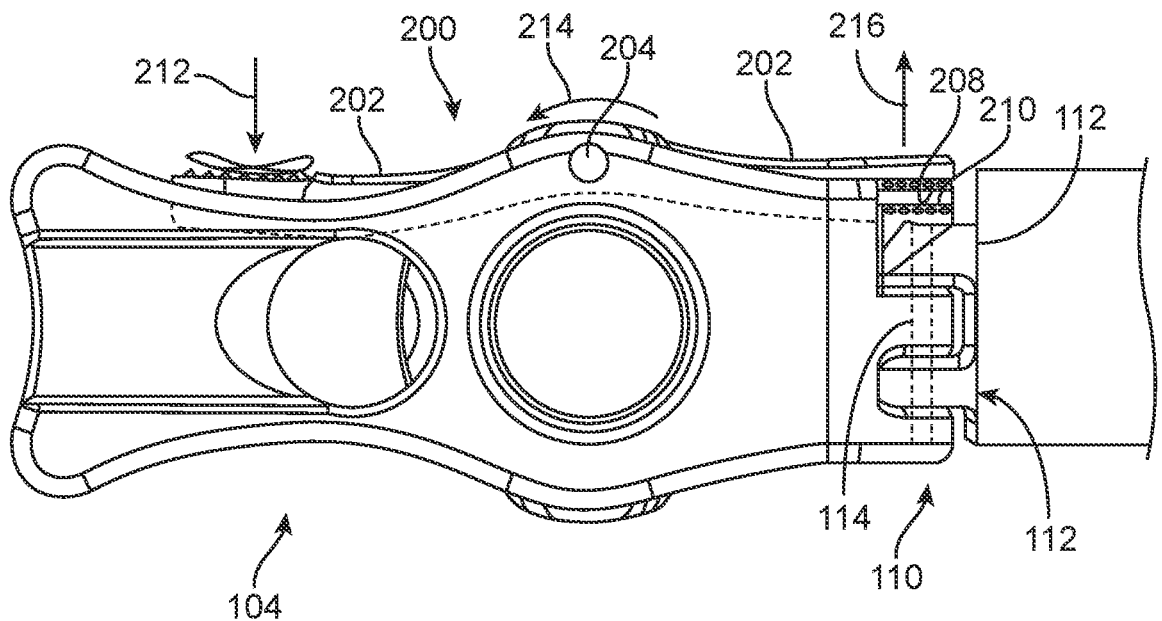

FIGS. 2A and 2B show an innovative left locking system 200 configured to lock the left connector 104 to the left end of the connecting member 108 that does not require secondary tightening, which allows for fast and high strength application of the crosslink 100 during surgery. The left locking system 200 includes a spring-loaded locking clip 202 positioned within a side recess or pocket 105 of the left connector 104. The spring-loaded locking clip 202 is coupled to the left connector 104 in a rocking or teeter-totter fashion with a pin 204. A first end 202a of the locking clip 202 includes a clip button 206 configured to be pushed, and a second end 202b includes radially engaging, interlocking teeth 208 configured to engage radially engaging, interlocking teeth 210 on the left connector hinge 112. The locking system 200 further includes a spring coupled to the locking clip 202 configured to position the locking clip 202 in a normally closed position. In the normally closed or locked position, the interlocking teeth 208 of the locking clip 202 are engaged with the interlocking teeth 210 of the left connector hinge 112, which locks the left connector 104 to the connecting member 108, preventing rotation of the left connector 104.

To unlock the locking system 200, the clip button 206 is compressed or pushed inward 212 toward the left connector 104, rocking 214 the locking clip 202, which moves the interlocking teeth 212 outward 216, disengaging the locking interlocking teeth 208 from the connecting member interlocking teeth 210.

To re-lock the left connector 104 with the connecting member 108, the clip button 206 is released, which moves the interlocking teeth 208 inward to reengage the connecting member interlocking teeth 210.

Figure 3A:
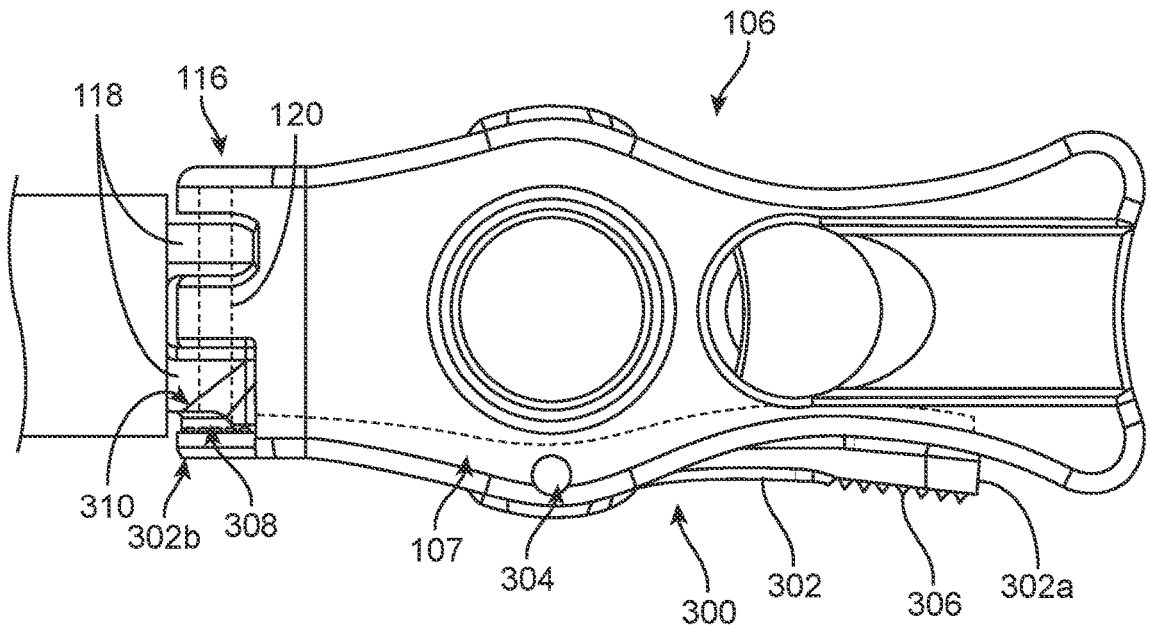
FIGS. 3A and 3B show a right locking system configured to lock the right connector to the right end of the connecting member.
Figure 3B:
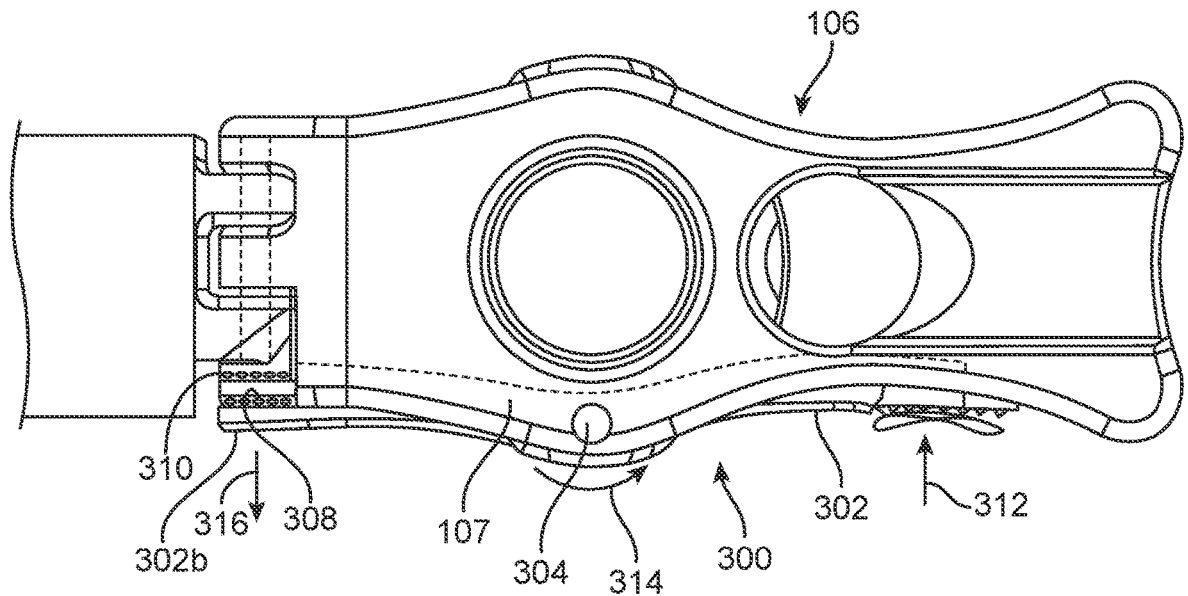

FIGS. 3A and 3B show a right locking system 300 configured to lock the right connector 106 to the right end of the connecting member 108. Locking system 300 is similar to locking system 200 discussed above. The locking system 300 includes a spring-loaded locking clip 302 positioned within a side recess or pocket 107 of the right connector 106. The spring-loaded locking clip 302 is coupled to the right connector 106 in a rocking or teeter-totter fashion with a pin 304. A first end 302a of the locking clip includes a clip button 306 configured to be pushed, and a second end 302b includes radially engaging, interlocking teeth 308 configured to engage radially engaging, interlocking teeth 310 on the right connector hinge 116. The locking system 300 further includes a spring coupled to the locking clip 302 configured to position the locking clip 302 in a normally closed or locked position. In the normally closed position, the interlocking teeth 308 of the locking clip 302 are engaged with the interlocking teeth 310 of the left connector hinge 112, which locks the right connector 106 to the connecting member 108, preventing rotation of the right connector 106.

To unlock the locking system 300, the clip button 306 is compressed or pushed inward 312 toward the right connector 106, rocking 314 the locking clip 302, which moves the interlocking teeth 308 outward 316, disengaging the locking interlocking teeth 308 from the connecting member interlocking teeth 310.

To re-lock the left connector 104 with the connecting member 108, the clip button 306 is released, which moves the interlocking teeth 308 inward to reengage the connecting member interlocking teeth 310.

The crosslink connection with reducers or extenders is rigid but not limited to clips as shown in the pictures.

Figure 4:
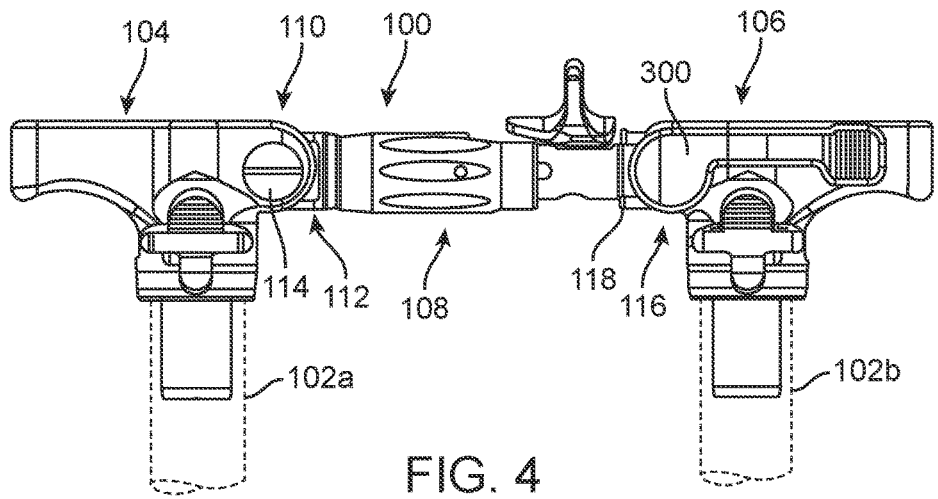
FIGS. 4, 5 and 6 show the left and right connectors being deployed in various orientations.
Figure 5:
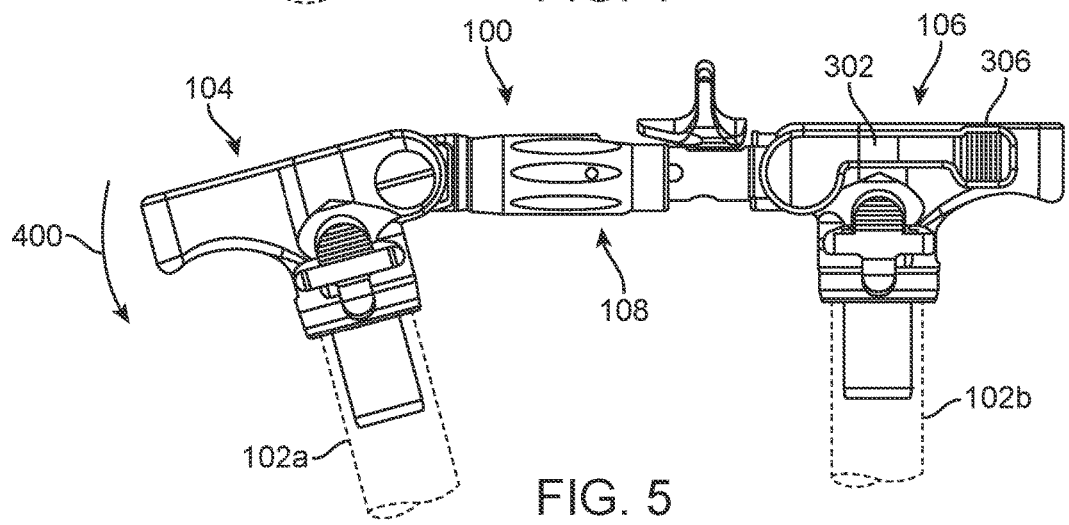
Figure 6:
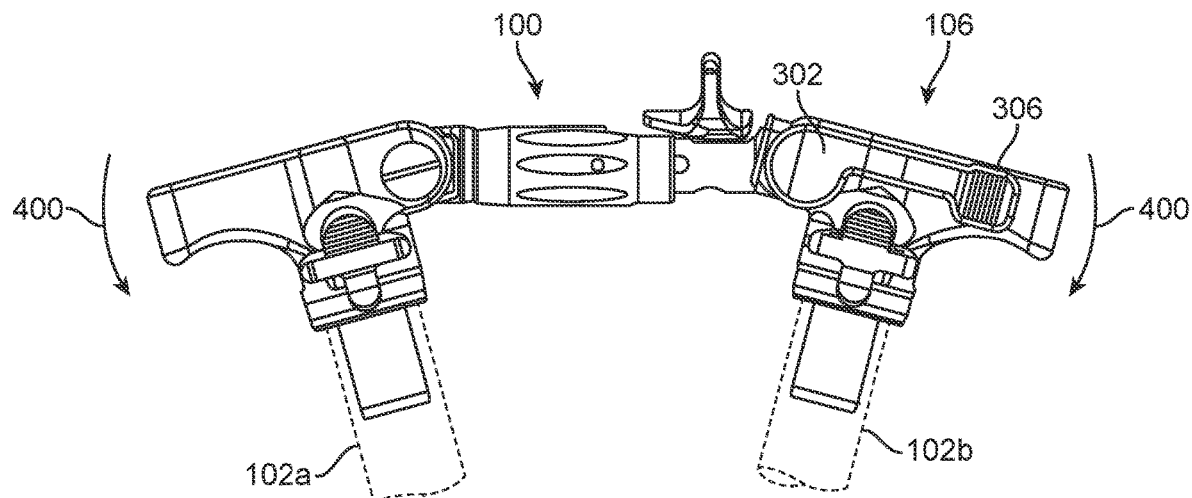

FIGS. 4, 5 and 6 show the left and right connectors 104, 106 being deployed in various orientations.

FIG. 4 shows a configuration for crosslink 100 in which both the left and right connector 104, 106 clipped onto the left and right sequential reducers 102a, 102b in a straight orientation with respect to the connecting member 108.

FIG. 5 shows a configuration for the crosslink 100 in which the left connector 104 are rotated 400 to a downward orientation with respect to the connecting member 108. To accomplish this rotation, the clip button 206 is pressed or compressed downward 212, which rocks the spring-loaded clip 202 and lifts the clip interlocking teeth 208 outward 216, disengaging the locking interlocking teeth 208 from the connecting member interlocking teeth 210 and unlocking the left connector 104. Once disconnected, the left connector 104 is free to rotate in a downward direction 400. The left connector 104 is then positioned in the desired orientation it is clipped onto the sequential reducer 102a. The clip button 206 is then released, allowing the spring to rock the spring-loaded clip 202 back into normal position with the interlocking teeth 208 lowering and coupling with the connecting member interlocking teeth 210, and therefore locking rotational freedom out of the mechanism.

FIG. 6 shows a configuration for the crosslink 100 in which the left and right connectors 104, 106 are rotated 400 to a downward orientation with respect to the connecting member 108. To accomplish this rotation for the left connector 104, the clip button 206 is pressed or compressed downward 212, which rocks the spring-loaded clip 202 and lifts the clip interlocking teeth 208 outward 216, disengaging the locking interlocking teeth 208 from the connecting member interlocking teeth 210 and unlocking the left connector 104. To accomplish this rotation for the right connector 106, the clip button 306 is pressed or compressed downward 312, which rocks the spring-loaded clip 302 and lifts the clip interlocking teeth 308 outward 316, disengaging the locking interlocking teeth 308 from the connecting member interlocking teeth 310 and unlocking the right connector 106.

Once disconnected, the left and right connectors 104, 106 are free to rotate in a downward direction 400. The left connector 104 is positioned in the desired orientation it is clipped onto the sequential reducer 102a. The clip button 206 is then released, allowing the spring to rock the spring-loaded clip 202 back into normal position with the interlocking teeth 208 lowering and coupling with the connecting member interlocking teeth 210 to lock the left connector 104. The right connector 106 is positioned in the desired orientation it is clipped onto the sequential reducer 102b. The clip button 306 is then released, allowing the spring to rock the spring-loaded clip 302 back into normal position with the interlocking teeth 308 lowering and coupling with the connecting member interlocking teeth 310 to lock the right connector 106.

In use, the reducers or extenders 102a, 102b, the left and right connectors 104, 106, and connecting member 108 are manipulated to desired or optimal position, then the locking systems 200, 300 are configured to lock the left and right connectors 104, 106, in the desired position with the connecting member 108 to hold the reducers or extenders 102a, 102b in a rigid structure or construct. Once locked, the crosslink 100 and reducers 102a, 102b may be rotated or moved as one body to correct a deformity.

Example embodiments of the methods and systems of the present invention have been described herein. As noted elsewhere, these example embodiments have been described for illustrative purposes only and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments but should be defined only in accordance with the following claims and their equivalents.

The invention claimed is:

1. A crosslink locking mechanism comprising:
a connector with a connector hinge with interlocking teeth;
a connecting member with a connecting member hinge with interlocking teeth rotatably couple with the connector hinge, the interlocking teeth of the connector hinge being coupled to the interlocking teeth of the connecting member in a normally locked position; and
a locking system includes a locking clip coupled to the connector in a rocking or teeter-totter fashion having a first end and a second end coupled to the interlocking teeth of the connector hinge being configured to lock and/or unlock the connector from the connecting member by moving the interlocking teeth of the connector hinge in relation to the interlocking teeth of the connecting member hinge, wherein the locking system is in a normally locked position preventing rotation with the interlocking teeth of the connector hinge engaged with the interlocking teeth of the connecting member hinge and pushing the first end down rocks the locking clip and moves the interlocking teeth up to unlock the connector.

2. The crosslink locking mechanism of claim 1, wherein the locking system is configured to unlock the connector by moving the interlocking teeth of the connector hinge away from the interlocking teeth of the connecting member to allow rotation of the connector.

3. The crosslink locking mechanism of claim 2, wherein the locking system is configured to relock rotation by moving the interlocking teeth of the connector hinge to reengage the interlocking teeth of the connecting member.

4. The crosslink locking mechanism of claim 1, wherein the connector is positioned in a desired orientation or position, the first end of the locking clip is released, allowing the locking clip to rock back into the locked position with the interlocking teeth of the connector lowering and coupling with the interlocking teeth of the connecting member to lock the connector.

5. The crosslink locking mechanism of claim 1, wherein the locking system includes a spring coupled to the locking clip configured to position the locking clip in a normally locked position.

6. The crosslink locking mechanism of claim 1, wherein the locking clip is positioned within a side recess or pocket of the connector.

7. A crosslink comprising:
a left connector having a left connector hinge with interlocking teeth;
a right connector having a right connector hinge with interlocking teeth;
a connecting member having a left connecting member hinge with interlocking teeth and a right connecting member hinge with interlocking teeth, the left connecting member hinge is configured to rotatably couple with the left connector hinge of the left connector and the right connecting member hinge is configured to rotatably couple with the right connector hinge of the right connector;
a left locking system coupled the interlocking teeth of the left connector being configured to lock/unlock rotation of the left connector hinge of the left connector with the left connecting member hinge of the connecting member; and
a right locking system coupled the interlocking teeth of the right connector being configured to lock/unlock rotation of the right connector hinge of the right connector with the right connecting member hinge of the connecting member.

8. The crosslink of claim 7, wherein the interlocking teeth of the left connector hinge are engaged with the interlocking teeth of the left connecting member hinge in a locked position which prevents rotation of the left connector with the left connecting member.

9. The crosslink of claim 8, wherein unlocking rotation includes the left locking system disengaging the interlocking teeth of the left connector away from the interlocking teeth of the left connecting member hinge.

10. The crosslink of claim 9, wherein relocking rotation includes the left locking system reengaging the interlocking teeth of the left connector with the interlocking teeth of the left connecting member hinge.

11. The crosslink of claim 7, wherein the left locking system includes a left locking clip coupled to the left connector in a rocking or teeter-totter fashion with a first end configured to be pushed and a second end configured to move the interlocking teeth.

12. The crosslink of claim 7, wherein the interlocking teeth of the right connector hinge are engaged with the interlocking teeth of the right connecting member hinge in a locked position which prevents rotation of the right connector with the right connecting member.

13. The crosslink of claim 12, wherein unlocking rotation includes the right locking system moving the interlocking teeth of the right connector away from the interlocking teeth of the right connecting member hinge.

14. The crosslink of claim 13, wherein relocking rotation includes the right locking system reengaging the interlocking teeth of the right connector with the interlocking teeth of the right connecting member hinge.

15. The crosslink of claim 7, wherein the right locking system includes a right locking clip coupled to the right connector in a rocking or teeter-totter fashion with a first end configured to be pushed and a second end configured to move the interlocking teeth.

16. The crosslink of claim 7, wherein the connecting member is configured to be shortened or extended with a locking mechanism configure to rigidly lock the length of the connecting member.

\* \* \* \* \*